(12) United States Patent
Anderson et al.

(10) Patent No.: US 10,398,892 B2
(45) Date of Patent: Sep. 3, 2019

(54) INTERVENTIONAL MEDICAL SYSTEMS AND ASSOCIATED ASSEMBLIES AND METHODS

(71) Applicant: Medtronic, Inc., Minneapolis, MN (US)

(72) Inventors: Thomas A. Anderson, New Hope, MN (US); Andrea J. Asleson, Maple Grove, MN (US); Michael D. Eggen, Chisago City, MN (US); McKenna Rose Redmond, Minneapolis, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 424 days.

(21) Appl. No.: 15/216,466

(22) Filed: Jul. 21, 2016

(65) Prior Publication Data

US 2018/0021571 A1 Jan. 25, 2018

(51) Int. Cl.
*A61N 1/05* (2006.01)
*A61B 17/34* (2006.01)
*A61N 1/375* (2006.01)

(52) U.S. Cl.
CPC ........ *A61N 1/0592* (2013.01); *A61B 17/3468* (2013.01); *A61N 1/3756* (2013.01); *A61N 1/37512* (2017.08)

(58) Field of Classification Search
CPC .............. A61N 1/0592; A61N 1/37512; A61N 1/3756; A61N 1/3758; A61B 17/34; A61B 17/3417; A61B 17/3468; A61M 25/0067; A61M 25/0074
See application file for complete search history.

(56) References Cited

U.S. PATENT DOCUMENTS

| | | | |
|---|---|---|---|
| 6,024,763 A | 2/2000 | Lenker et al. | |
| 6,355,060 B1 | 3/2002 | Lenker et al. | |
| 6,814,746 B2 | 11/2004 | Thompson et al. | |
| 7,771,444 B2 | 8/2010 | Patel et al. | |
| 8,469,979 B2 | 1/2013 | Olson | |
| 8,831,741 B2 * | 9/2014 | Griswold | A61M 25/0074 604/508 |
| 2005/0209619 A1 * | 9/2005 | Johnson | A61B 17/34 606/167 |
| 2006/0095030 A1 * | 5/2006 | Avitall | A61B 18/1492 606/41 |

(Continued)

*Primary Examiner* — Sarah W Aleman

(57) ABSTRACT

A catheter assembly includes a cap and a spring-biased tethering member coupled thereto. The cap includes first and second portions, and a transition zone extending therebetween. A girth of the first portion is sized to fit within a distal-most opening of the catheter assembly; and a girth of the second portion tapers from a first size at the transition zone, which is too large to fit within the distal-most opening, to a smaller size at a distal end of the cap. The spring-biased tethering member holds the cap in open and closed positions, when the cap first portion extends within the distal-most opening, and when the cap is separated from the distal-most opening, respectively. At the closed position, the first portion is approximately concentric with the distal-most opening, and at the open position, an entirety of the cap is laterally offset from the distal-most opening.

22 Claims, 5 Drawing Sheets

(56) References Cited

U.S. PATENT DOCUMENTS

| | | | |
|---|---|---|---|
| 2008/0021532 A1* | 1/2008 | Kveen | A61N 1/0573 |
| | | | 607/115 |
| 2011/0040283 A1 | 2/2011 | Harris | |
| 2012/0172690 A1 | 7/2012 | Anderson | |
| 2015/0094668 A1 | 4/2015 | Wood et al. | |

* cited by examiner

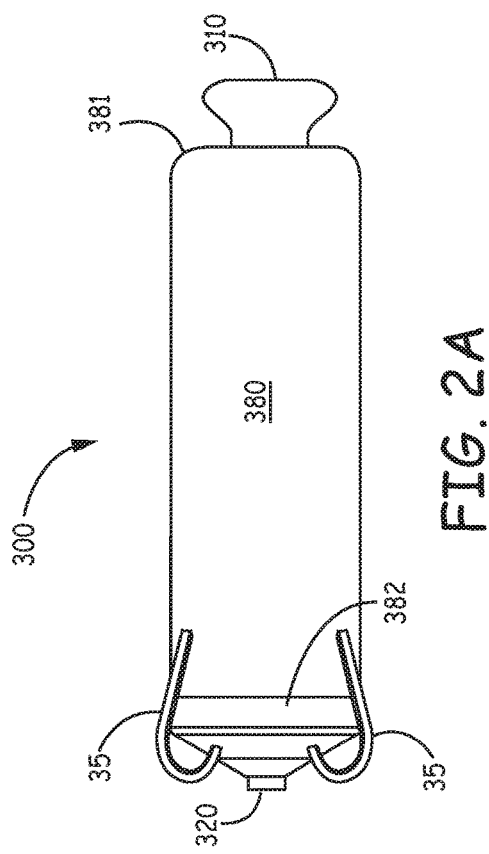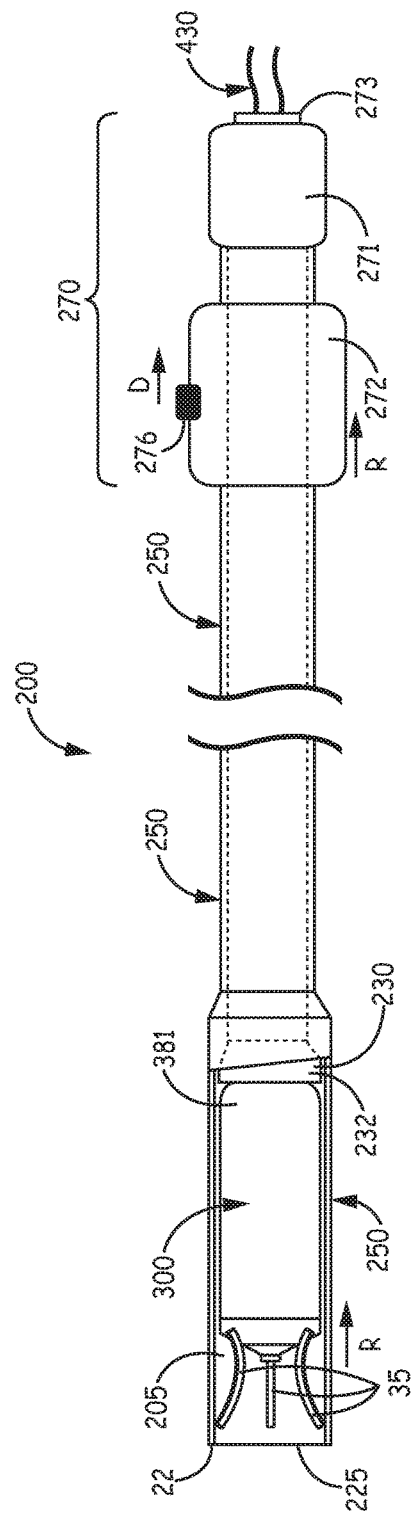

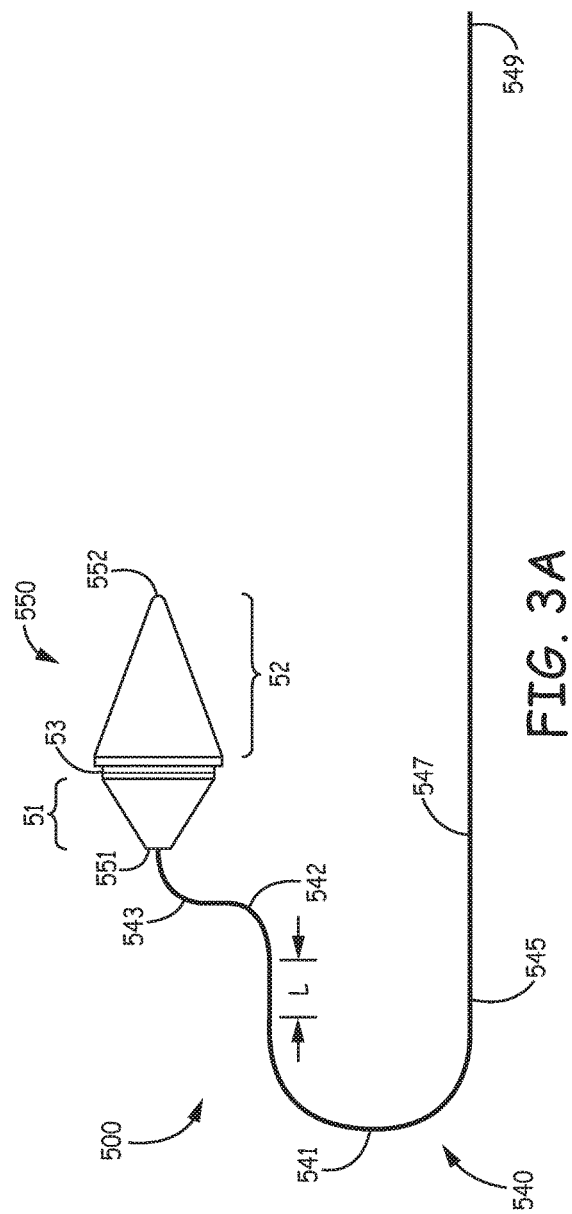
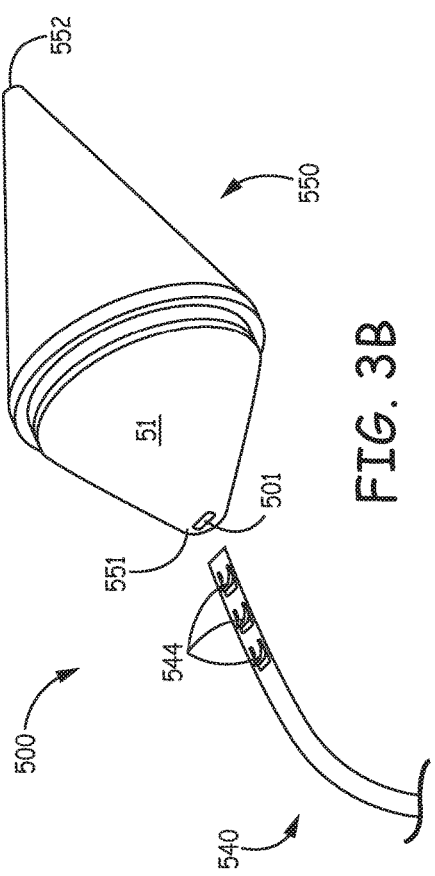

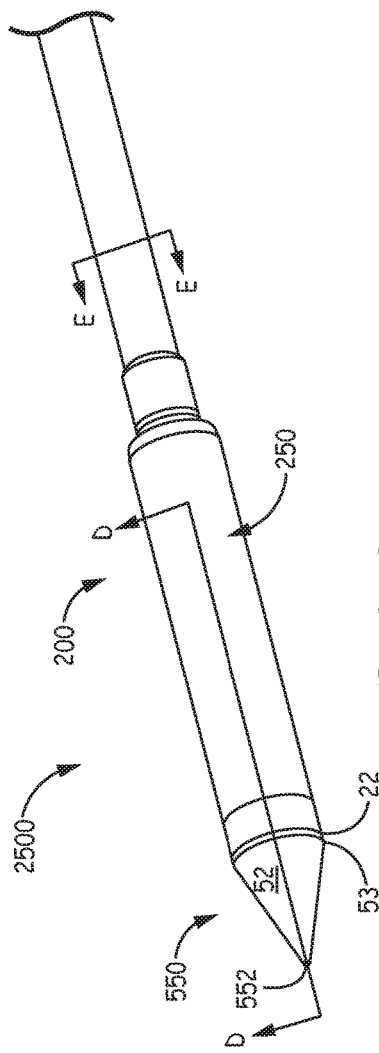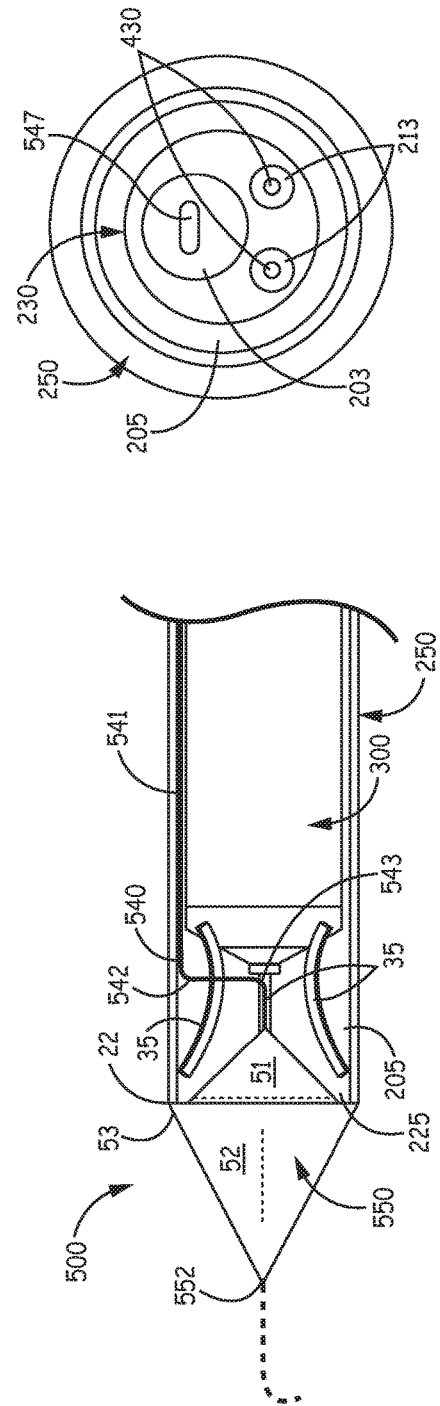

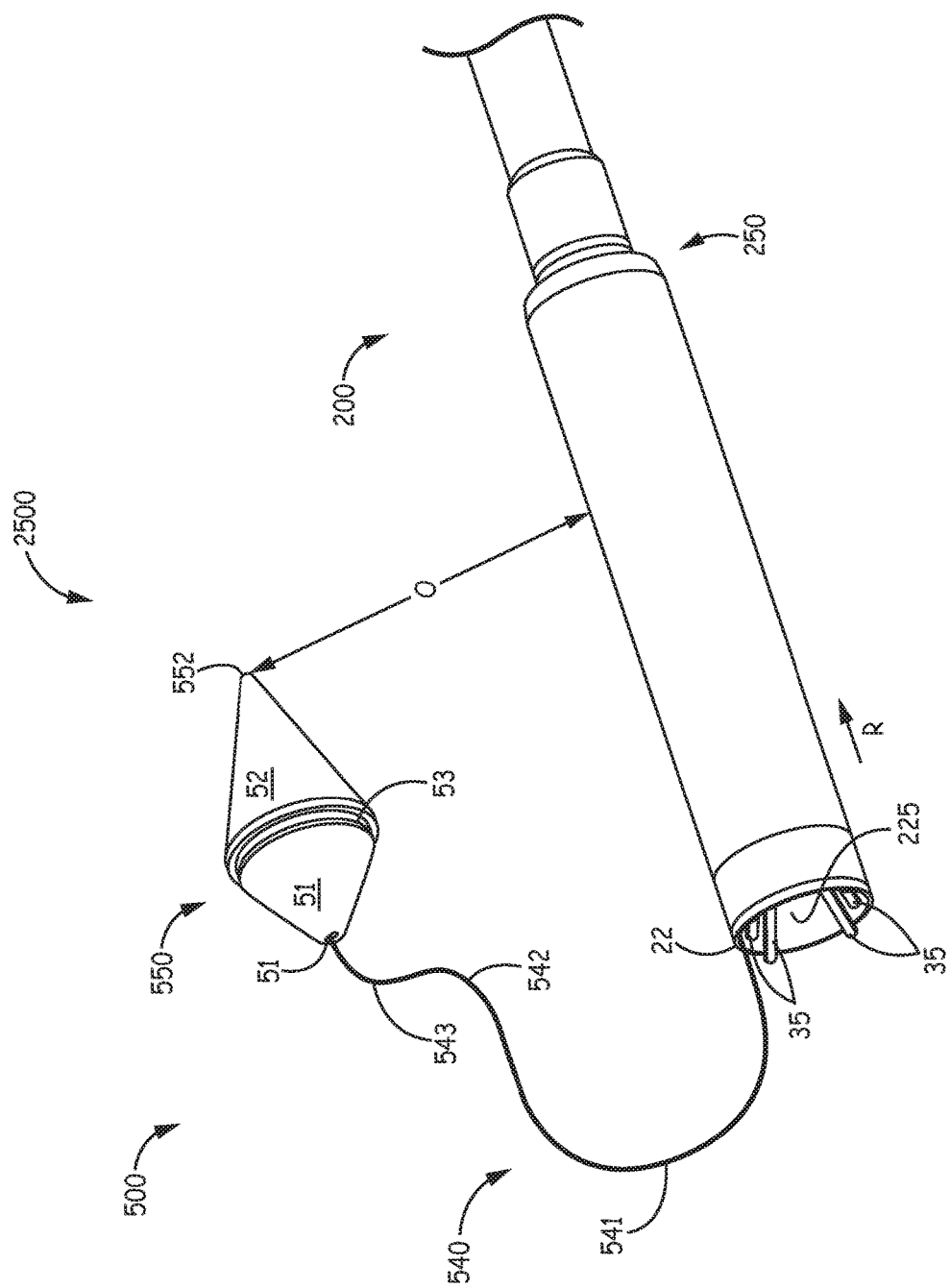

INTERVENTIONAL MEDICAL SYSTEMS AND ASSOCIATED ASSEMBLIES AND METHODS

FIELD OF THE DISCLOSURE

The present disclosure pertains to interventional medical systems, and more particularly to catheter assemblies thereof that are used to deliver relatively compact implantable medical devices to an implant site.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. Such a medical device and a corresponding catheter assembly that is configured as a delivery tool for the device are described in the commonly assigned United States Patent Application US 2015/0094668. A schematic diagram in FIG. 1 shows potential cardiac implant sites to which the described delivery tool may deliver the device, for example, within an appendage 102 of a right atrium RA, or in proximity to an apex 103 of a right ventricle RV.

With further reference to FIG. 1, alternative implant sites for the device are on the left side of the heart, for example, within a coronary vein CV, which may be accessed through a coronary sinus ostium CSOS, or within the left ventricle (not seen), which may be accessed through an orifice created through (into the page) an interatrial septum IS in the area of appendage 102. But an operator may encounter some difficulty in navigating a catheter assembly/delivery tool like that described in the '668 reference to these sites on the left side of the heart.

SUMMARY

Embodiments of interventional medical systems, disclosed herein, include a relatively compact implantable medical device and a catheter assembly, wherein the catheter assembly includes an end-cap subassembly that facilitates the navigation of the catheter assembly through blood vessels and/or orifices, for example, to deliver the implantable medical device to a left side of a patient's heart. The end-cap subassembly, according to embodiments disclosed herein, includes a cap and a spring-biased tethering member, which is secured to the catheter assembly, and which is coupled to the cap.

According to some embodiments, the cap includes a first portion, a second portion, and a transition zone that extends between the first and second portions, wherein the first portion has a girth sized to fit within a distal-most opening of a lumen of the catheter assembly, and the second portion has a girth that tapers from a first size at the transition zone, which is too large to fit with the distal-most opening, to a smaller second size at a distal end of the cap. The transition zone may define an edge that abuts a distal terminal end of the catheter assembly when the first portion is fitted within the distal-most opening. The spring-biased tethering member extends from a proximal end of the cap and is configured to hold the cap in a closed position and in an open position: the closed position being that at which the first portion of the cap is approximately concentric with the distal-most opening of the lumen, when the first portion of the cap extends within the distal-most opening of the lumen of the catheter assembly; and the open position being that at which an entirety of the cap is laterally offset from the distal-most opening, when the cap is separated from the distal-most opening of the lumen and the spring-biased tethering member extends out from the distal-most opening.

According to some embodiments and methods, the spring-biased tethering member of the end-cap subassembly is made, at least in part, from a super-elastic wire having a curvature formed therein; and a distal end of the wire is coupled to the cap so that the curvature extends in close proximity to the proximal end of the cap. After securing the tethering member to the catheter assembly and loading the medical device into the lumen of the catheter assembly, the first portion of the cap is positioned within the lumen of the catheter assembly, so that the coupled super-elastic wire extends alongside the loaded device in the lumen, the edge defined by the cap transition zone abuts the distal terminal end of the catheter assembly, and the second portion of the cap extends distally from the distal terminal end.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 2A is a plan view of an exemplary relatively compact implantable medical device that may be included in systems of the present invention, according to some embodiments;

FIG. 2B is a plan view, which includes a partial cross-section, of an exemplary interventional medical system;

FIG. 3A is a plan view of an end-cap subassembly, according to some embodiments;

FIG. 3B is an exploded perspective view of a portion of the end-cap subassembly, according to some embodiments;

FIG. 3C is a perspective view of an interventional medical system, according to some embodiments of the present invention;

FIG. 3D is a cross-section view through section line D-D of FIG. 3C, according to some embodiments;

FIG. 3E is a cross-section view through section line E-E of FIG. 3C, according to some embodiments; and FIG. 4 is another perspective view of the system, according to some embodiments.

DETAILED DESCRIPTION

Figure 1:
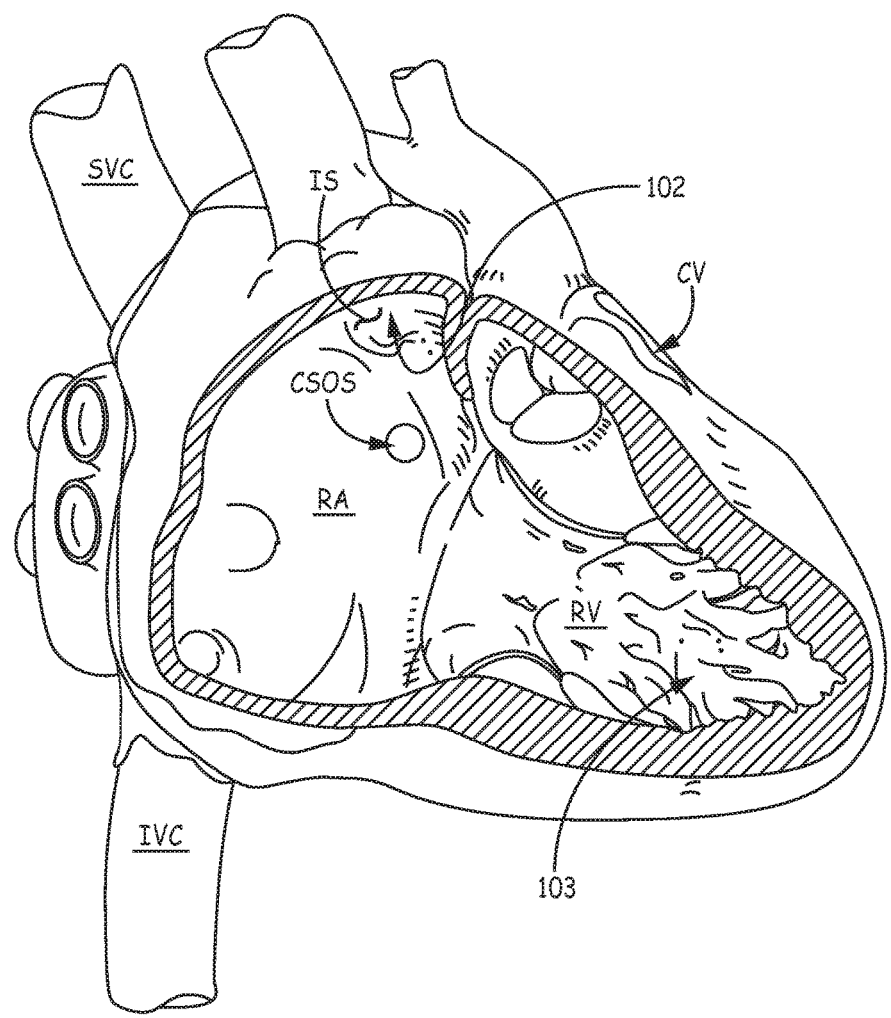
FIG. 1 is a schematic diagram showing potential implant sites for a relatively compact implantable medical device.

The following detailed description is exemplary in nature and is not intended to limit the scope, applicability, or configuration of the invention in any way. Rather, the following description provides practical examples, and those skilled in the art will recognize that some of the examples may have suitable alternatives.

FIG. 2A is a plan view of an exemplary relatively compact implantable medical device 300 that may be included in systems of the present invention, according to some embodiments. FIG. 2A illustrates medical device 300 including a hermetically sealed housing 380, which extends from a proximal end 381 thereof to a distal end 382 thereof, and an electrode 320, which is mounted to housing distal end 382. According to the illustrated embodiment, an electronic controller (not shown), for example, a pulse generator and an associated power supply, are contained within housing 380, and electrode 320 is electrically coupled to the controller via a hermetically sealed feedthrough assembly (not shown) such as is known in the art.

Device 300 further includes a fixation member, for example, formed by a plurality of super-elastic fingers 35 spaced apart from one another around a perimeter of housing distal end 382. Although only two fixation fingers 35 are shown in FIG. 3A, device 300 may include as many as eight. According to an exemplary embodiment, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art. Fixation fingers 35 may be mounted to distal end 382 of device housing 380, for example, in a manner similar to that described for a fixation component 102 in a commonly assigned United States Patent Application 2012/0172690, which description is hereby incorporated by reference. The super-elastic nature of Nitinol allows fingers 35 to elastically deform between a relaxed condition, which is shown, and an extended condition, in which a free end of each finger extends distally away from distal end 382 of device housing 380, for example, when device 300 is loaded into a catheter assembly 200, as shown in FIG. 2B. According to the illustrated embodiment, fixation fingers 35 are configured to pierce into tissue at the implant site and thereby secure electrode 320 in intimate tissue contact. In some embodiments, device 300 preferably includes a steroid-eluting member (not shown), for example, mounted in, or around electrode 320, which is useful for reducing inflammation of the pierced tissue to maintain effective and efficient pacing via electrode 320.

Device housing 380, for example, formed from a biocompatible and biostable metal such as titanium, may be overlaid with an insulative layer, for example, medical grade polyurethane, parylene, or silicone, and, although not shown, device 300 may include another electrode, for example, formed by removing a portion of the insulative layer to expose the metallic surface of housing 380. The other electrode may function in conjunction with electrode 320 for bipolar pacing and sensing.

FIG. 2A further illustrates device 300 including a holding member 310 joined to housing proximal end 381 and protruding proximally therefrom to form a proximal end of device 300. Holding member 310 may have any suitable configuration for securing device 300 to a catheter, for example, by means of a tether 430 that extends within an elongate inner tubular member 230 of catheter assembly 200 and out from a proximal port opening 273 of assembly 200 (FIGS. 2B and 3E). FIG. 2B, is a plan view, with a partial cross-section, of an exemplary system including device 300 and catheter assembly 200. FIG. 2B illustrates inner tubular member 230 (dashed lines) extending within a lumen 205 of an elongate outer tubular member 250 of catheter assembly 200, and a distal end 232 of inner tubular member 230 engaging with the proximal end/holding member 310 of device 300, when device 300 is contained within lumen 205 of outer tubular member 250. FIG. 2B further illustrates catheter assembly 200 including a handle 270, which has a distal portion 272 coupled to a proximal end of outer tubular member 250, and a proximal portion 271 coupled to a proximal end of inner tubular member 230, wherein proximal portion 271 includes proximal port opening 273. Outer tubular member 250 is moveable relative to inner tubular member 230, via handle distal portion 272, between an advanced position (shown) and a retracted position, per arrow R. A distal terminal end 22 of outer tubular member 250 is shown defining a distal-most opening 225 of lumen 205, which allows passage of device 300 therethrough, for loading device 300 into catheter assembly 200, and for deploying device 300 to an implant site, when outer tubular member 250 is moved to the retracted position, per arrow R.

With further reference to FIG. 2B, a control member 276 for an optional steering assembly of catheter assembly 200 is shown being mounted to handle distal portion 272. The steering assembly, according to configurations known in the art, may further include a pull band mounted on outer tubular member 250 and an elongate pull wire that extends along a length of outer tubular member 250, being coupled, at a distal end thereof, to the pull band and, at a proximal end thereof, to control member 276. Moving control member 276, per arrow D, causes the pull wire to deflect outer tubular member 250, along with inner tubular member 230 and device 300, which may be useful in navigating the system into proximity with an implant site. However, with reference back to FIG. 1, if the implant site is located on the left side of a patient's heart, for example, within coronary vein CV, being accessed through coronary sinus ostium CSOS, or within the left atrium (not seen), being accessed through an orifice created through (into the page) interatrial septum IS, an operator may find it difficult to pass distal terminal end 22 of outer tubular member 250 through ostium CSOS or the created interatrial orifice. But, to alleviate this difficulty, a tapering leading edge for catheter assembly 200 is provided by an end-cap subassembly 500, according to some embodiments of the present invention. FIG. 3A is a plan view of end-cap subassembly 500, according to some embodiments; and FIG. 3C is a perspective view of an interventional medical system 2500, in which catheter assembly 200 includes subassembly 500.

FIG. 3A illustrates end-cap subassembly 500 including a cap 550 and a spring-biased tethering member 540 coupled to cap 550 and extending from a proximal end 551 of cap 550. Cap 550 is shown including a first portion 51, a second portion 52, and a transition zone 53 extending therebetween, wherein first portion 51 has a girth sized to fit within distal-most opening 225 of lumen 205 of outer tubular member 250 (FIG. 2B), and transition zone 53 defines an edge that abuts distal terminal end 22 of outer tubular member 250, when cap first portion 51 is fitted within distal-most opening 225, as shown in FIG. 3C. FIGS. 3A and 3C further illustrate cap second portion 52 having a girth that tapers from a first size, at transition zone 53, which is too large to fit within distal-most opening 225, to a second, smaller size at a distal end 552 of cap 550, to form the leading edge that can facilitate the passage of system 2500 through a vein or orifice to the left side of a patient's heart. The girth of cap first portion 51 is also shown tapering from a larger size in proximity to transition zone 53 to a smaller size at cap proximal end 551, which may facilitate the positioning of cap first portion 51 within distal-most opening 225 of outer tubular member lumen 205. Although cap portions 51, 52 are both shown tapering to a point at respective ends 551, 552 of cap 550, ends 551, 552 may be relatively flat or rounded in alternate embodiments.

With further reference to FIG. 3A, spring-biased tethering member 540 of end-cap subassembly 500 includes a distal segment formed by a super-elastic wire that has a pre-formed curvature, which is shown in a relaxed, or biased state. FIG. 3A illustrates the pre-formed curvature including a series of bends 541, 542, 543 configured to hold cap 550 in a closed position (FIGS. 3C-D), and in an open position (FIG. 4), which are described in greater detail below. According to the illustrated embodiment, bend 541 extends around approximately 180 degrees, and each of bends 542, 543 extends around approximately 90 degrees. In FIG. 3D, which is a cross-section view through section line D-D of FIG. 3C, spring-biased tethering member 540 is shown with the pre-formed curvature thereof deformed to extend alongside device 300, within lumen 205 of outer tubular member 250.

FIG. 3A further illustrates tethering member 540 including an elongate proximal segment 547 to which a proximal end 545 of the distal segment with the pre-formed curvature is coupled. With reference to the cross-section view of FIG. 3E, segment 547 extends within a lumen 203 of inner tubular member 230, wherein proximal segment 547 may have a length approximately equal to that of inner tubular member 230 of catheter assembly 200 so that a proximal end 549 of end-cap subassembly 500 extends through handle proximal portion 271 and out from proximal port opening 273 (FIG. 2B). According to some embodiments, proximal segment 547 is integral with, and an extension of the super-elastic wire that forms the distal segment of spring-biased tethering member 540, but, according to some alternate embodiments, proximal segment 547 is formed by a separate elongate rod. In either case, spring-biased tethering member 540 may be secured to catheter assembly by threading proximal segment through lumen 203 of inner tubular member 230.

With further reference to FIG. 3A, cap 550 of end-cap subassembly 500 may be formed from a relatively hard medical grade plastic, such as polyurethane, nylon, polyether ether ketone (PEEK), or acrylonitrile butadiene styrene (ABS); and the super-elastic wire of spring-biased holding member 540, for example, being a medical grade Nitinol, has a rectangular cross-section, for example, being approximately 0.005 inch by 0.025 inch. According to an exemplary embodiment, bend 541 has a radius of approximately 0.25 inch, and each of bends 542, 543 has a radius of approximately 0.125 inch, wherein a relatively straight length L of the super-elastic wire between bend 541 and bend 542 is approximately 0.160 inch. The curvature of spring-biased holding member 540 may be shaped by bending and holding the super-elastic wire while heat treating, according to methods known in the art. Tethering member 540 may be coupled to cap 550 by interlocking engagement therewith, for example, via tabs 544 shown in the exploded perspective view of FIG. 3B. FIG. 3B illustrates three outward-bending tabs 544, which are integrally formed in an end of the super-elastic wire of tethering member 540, and which are configured to engage within an internal channel of cap 550, when the end is pushed into an opening 501 of the channel. Alternately, cap 550 may include a cross-hole (not shown) in communication with the channel, wherein a locking pin passed through the cross-hole intersects with the inserted end of the super-elastic wire to lock it in place within the channel. Alternately, holes may be formed through the end of the super-elastic wire, in lieu of tabs 544, and an adhesive material, injected into the channel, may be employed to form an interlocking adhesive bond between tethering member 540 and cap 550.

With further reference to FIG. 3D, end-cap subassembly 500 may further include at least one radiopaque marker, for example, a platinum/iridium, gold, or tungsten band extending around cap transition zone 53, and/or a platinum/iridium, gold, or tungsten pin extending within cap second portion 52, both of which are shown with dashed lines. FIG. 3D further illustrates end-cap subassembly 500 including an optional atraumatic guide-wire tip (bold dashed line), which is coupled to cap 550 and extends distally from cap distal end 552, and which may be pre-formed by an operator to facilitate the aforementioned passage of system 2500 to the left side of the patient's heart.

An exemplary construction of other members of catheter assembly 200 may be as follows. Outer tubular member 250, for example, extending over a length of approximately 100 cm, may be formed by a stainless steel braid-reinforced medical grade polymer, for example, one or more appropriate grades of polyether block amide, which are arranged for decreasing stiffness from handle 270 to distal terminal end 22 of tubular member 250 (e.g., including PEBAX® 3533, 6333, 4033, and 7233); and lumen 205 of tubular member 250 may have a diameter of approximately 0.3 inch (7.6 mm) in proximity to distal-most opening 225, to contain medical device 300 therein. Outer tubular member 250, in proximity to distal terminal end 22, may have a radiopaque filler blended therein, or a radiopaque marker (e.g., Tungsten-filled Vestamid®) bonded thereto, either according to methods known to those skilled in the art. Inner tubular member 230 may be formed from a medical grade polymer, such as extruded polyether block amide, polyurethane, or silicone rubber, or a composite thereof, and have multiple lumens 203, 213, for example, being arranged as shown in FIG. 3E, and extending along a length of inner tubular member 230. Tubular member 230 may further include an overlay (not shown), for example, formed of braid-reinforced polyether block amide. With further reference to FIG. 3E, the aforementioned tether 430, which secures device 300 to catheter assembly 200, extends within lumens 213, wherein tether 430 is looped around device holding member 310 and opposing ends thereof extend out from proximal port opening 273 of assembly 200. Handle 270 may be constructed from injection molded, relatively hard, medical grade plastic parts, according to methods known in the art.

According to some methods, the operator loads device 300 into catheter assembly 200 while spring-biased holding member 540 extends out from distal-most opening 225 of outer tubular member 250, with bends 541, 542, 543 thereof un-deformed, as shown in FIG. 3A, to hold cap 550 in the open position, separated from distal-most opening 225, so that an entirety of cap 550 is laterally offset from distal-most opening 225, to make way for passage of device 300 into lumen 205 through opening 225. After device 300 is loaded into catheter assembly 200, the operator can move cap 550 of end-cap subassembly 500 to the closed position, which is shown in FIGS. 3C-D. FIG. 3D illustrates cap 550 having been moved to the closed position, such that bend 541 of tethering member 540 is deformed (approximately straightened) and extends alongside device 300 within lumen 205 of outer tubular member 250 of catheter assembly 200, while bends 542 and 543 of tethering member 540 hold cap first portion 51 within lumen 205, approximately concentric with distal-most opening 225, by the spring-bias of member 540. With further reference to FIG. 3A, proximal end 549 of end-cap subassembly 500 extends out from proximal port opening 273 of catheter assembly 200 (FIG. 2B), as described above, so that the operator may grasp proximal end 549 to apply push and pull forces through proximal segment 547 of end-cap subassembly 500 to move cap 550 between the open and closed positions, respectively.

After the operator has loaded device 300 into catheter assembly 200, and has navigated system 2500 to an implant site, for example, on the left side of the patient's heart, at either of the locations described above in conjunction with FIG. 1, the operator manipulates catheter assembly 200 to separate cap 550 from distal-most opening 225 of outer tubular member 250, so that spring-biased holding member 540 holds cap 550 in the open position which is shown in FIG. 4. FIG. 4 illustrates the above-described open position, at which an entirety of cap 550 is laterally offset from distal-most opening 225, for example, by a distance O of approximately 0.76 inch, to make way for the passage of device 300 therethrough for deployment to the implant site. In embodiments of catheter assembly 200 that include end-cap subassembly 500, the operator can grasp proximal end 549 of spring-biased tethering member 540, which extends proximally from catheter assembly proximal port opening 273 (FIG. 2B), to apply a push force through proximal segment 547 of subassembly 500 to force spring-biased tethering member 540 and cap 550 out from distal-most opening 225, prior to moving outer tubular member 250, per arrow R, to the retracted position, at which device fixation fingers 35 are exposed to engage tissue at the implant site. After fixation fingers 35 are engaged with the tissue at the implant site, tether 430 is released from device holding member 310 before withdrawing catheter assembly 200 from the patient. Prior to withdrawing catheter assembly 200, the operator may return cap 550 to the closed position, for example, by applying a pull force to proximal segment 547 of end-cap subassembly 500.

In the foregoing detailed description, the invention has been described with reference to specific embodiments. However, it may be appreciated that various modifications and changes can be made without departing from the scope of the invention as set forth in the appended claims.

We claim:

1. An interventional medical system comprising an implantable medical device and a catheter assembly;
   the implantable medical device comprising an electronic controller, a hermetically sealed housing containing the controller, an electrode electrically coupled to the controller, and a fixation member mounted to a distal end of the housing;
   the catheter assembly comprising an elongate inner tubular member, an elongate outer tubular member, and an end-cap subassembly;
   the outer tubular member defining an elongate lumen in which the inner tubular member extends, the outer tubular member extending from a proximal end of the outer tubular member to a distal terminal end of the outer tubular member, the distal terminal end of the outer tubular member defining a distal-most opening of the elongate lumen, the elongate lumen, in proximity to the distal-most opening, being sized to contain an entirety of the implantable medical device therein, and the distal-most opening allowing passage of the implantable medical device therethrough;
   the inner tubular member including a distal end of the inner tubular member configured to engage with a proximal end of the implantable medical device, and the inner tubular member being moveable through the elongate lumen defined by the outer tubular member; and
   the end-cap subassembly of the catheter assembly comprising:
      a cap including a proximal end of the cap, a distal end of the cap, a first portion extending from the proximal end of the cap, a second portion extending from the distal end of the cap, and a transition zone extending between the first and second portions, the first portion having a girth sized to fit within the distal-most opening of the lumen of the outer tubular member, the second portion having a girth that tapers from a first size at the transition zone to a second, smaller size at the distal end, the girth of the second portion at the transition zone being too large to fit within the distal-most opening of the elongate lumen defined by the outer tubular member; and
      a spring-biased tethering member extending within the catheter assembly, a distal end of the spring-biased tethering member being coupled to the cap so that the tethering member extends from the proximal end of the cap, the tethering member being configured extend alongside the implantable medical device when the implantable medical device is contained in the lumen of the outer tubular member; and
   wherein, when the first portion of the cap extends within the distal-most opening of the elongate lumen of the outer tubular member, the catheter assembly constrains the spring-biased tethering member in a spring-loaded first configuration;
   wherein, when the outer tubular member is retracted relative to the spring-biased tethering member the cap is separated from the distal-most opening of the elongate lumen of the outer tubular member and the spring-biased tethering member is released to extend out from the distal-most opening and to a second configuration in which the spring-biased tethering member holds the cap in an open position, at which an entirety of the cap is laterally offset from the distal-most opening; and
   wherein, when in the second configuration, the spring-biased tethering member has a pre-formed curvature comprising a plurality of bends, at least two of the plurality of bends in different directions.

2. The system of claim 1, wherein the spring-biased tethering member of the end-cap subassembly of the catheter assembly comprises a proximal segment and a distal segment, the proximal segment having a length approximately equal to that of the inner tubular member and being in sliding engagement within a lumen of the inner tubular member, and the distal segment having the pre-formed curvature.

3. The system of claim 1, wherein spring-biased tethering member comprises a super-elastic wire having the pre-formed curvature.

4. The system of claim 3, wherein the super-elastic wire of the spring-biased tethering member has a rectangular cross-section.

5. The system of claim 1, wherein the pre-formed curvature comprises a first bend, a second bend closer to the distal end of the spring-biased tethering member than the first bend, and a third bend closer to the distal end of the spring-biased tethering member than the second bend, the first bend extending around approximately 180 degrees, and each of the second and third bends extending around approximately 90 degrees.

6. The system of claim 1, wherein the end-cap subassembly of the catheter assembly further comprises a radiopaque marker extending around the transition zone of the cap.

7. The system of claim 1, wherein the end-cap subassembly of the catheter assembly further comprises a radiopaque marker extending within the second portion of the cap.

8. The system of claim 1, wherein the end-cap subassembly of the catheter assembly further comprises an atraumatic guide-wire tip being coupled to the cap and extending distally from the distal end of the cap.

9. The system of claim 1, wherein the transition zone of the cap defines an edge that abuts the distal terminal end of the outer tubular member of the catheter assembly when the first portion of the cap is fitted within the distal-most opening of the elongate lumen defined by the outer tubular member.

10. The system of claim 1, wherein the plurality of bends comprises a first bend and a second bend closer to the distal end of the spring-biased tethering member than the first bend, wherein a direction of the second bend is opposite a direction of the first bend.

11. An end-cap subassembly for a catheter assembly, the end-cap subassembly comprising:
a cap including a proximal end of the cap, a distal end of the cap, a first portion extending from the proximal end of the cap, a second portion extending from the distal end, and a transition zone extending between the first and second portions, the first portion having a girth sized to fit within a distal-most opening of a lumen of the catheter assembly, the second portion having a girth that tapers from a first size at the transition zone to a smaller, second size at the distal end, the girth of the second portion at the transition zone being too large to fit within the distal-most opening of the lumen defined by the catheter assembly; and
a spring-biased tethering member coupled to the cap and extending from the proximal end of the cap, the spring-biased tethering member being configured extend within the catheter assembly alongside an implantable medical device that is contained within the lumen;
wherein, when the first portion of the cap extends within the distal-most opening of the lumen of the catheter assembly, the catheter assembly constrains the spring-biased tethering member in a spring-loaded first configuration;
wherein, when the spring-biased tethering member extends out from the distal-most opening of the catheter assembly, the spring-biased tethering member is released to a second configuration in which the spring-biased tethering member holds the cap in an open position, the open position being that at which an entirety of the cap is laterally offset from the distal-most opening; and
wherein, when in the second configuration, the spring-biased tethering member has a pre-formed curvature comprising a plurality of bends, at least two of the plurality of bends in different directions.

12. The subassembly of claim 11, wherein spring-biased tethering member comprises a super-elastic wire having the pre-formed curvature.

13. The subassembly of claim 12, wherein the super-elastic wire of the spring-biased tethering member has a rectangular cross-section.

14. The subassembly of claim 11, wherein the pre-formed curvature comprises a first bend, a second bend closer to the distal end of the spring-biased tethering member than the first bend, and a third bend closer to the distal end of the spring-biased tethering member than the second bend, the first of the three bend extending around approximately 180 degrees, and each of the second and third bends extending around approximately 90 degrees.

15. The subassembly of claim 11, further comprising a radiopaque marker extending around the transition zone of the cap.

16. The subassembly of claim 11, further comprising a radiopaque marker extending within the second portion of the cap.

17. The subassembly of claim 11, further comprising an atraumatic guide-wire tip being coupled to the cap and extending distally from the distal end of the cap.

18. The subassembly of claim 11, wherein the transition zone of the cap defines an edge that abuts a distal terminal end of the catheter assembly when the first portion of the cap is fitted within the distal-most opening of the lumen defined by the catheter assembly.

19. The subassembly of claim 11, wherein the plurality of bends comprises a first bend and a second bend closer to the distal end of the spring-biased tethering member than the first bend, wherein a direction of the second bend is opposite a direction of the first bend.

20. A method for assembling an interventional medical system, the method comprising:
forming a curvature in a super-elastic wire, the curvature comprising a plurality of bends, at least two of the plurality of bends in different directions;
securing the super-elastic wire to a catheter assembly;
coupling the super-elastic wire to a cap so that the formed curvature extends in close proximity to a proximal end of the cap;
loading an implantable medical device into a lumen of the catheter assembly, through a distal-most opening of the catheter assembly; and
positioning a first portion of the cap within the distal-most opening of the catheter assembly, so that the coupled super-elastic wire extends alongside the loaded implantable medical device in the lumen, and a second portion of the cap extends distally from a distal terminal end of the catheter assembly defining the distal-most opening of the catheter assembly.

21. The method of claim 20, wherein securing the super-elastic wire to the catheter assembly comprises threading the super-elastic wire through an inner tubular member of the catheter assembly.

22. The method of claim 20, wherein securing the super-elastic wire to the catheter assembly comprises coupling the wire to an elongate rod and then threading the rod through an inner tubular member of the catheter assembly.

* * * * *